United States Patent
Van Der Bos

(10) Patent No.: US 9,540,120 B2
(45) Date of Patent: Jan. 10, 2017

(54) DROP TEST DEVICE AND METHOD FOR CARRYING OUT A DROP TEST

(71) Applicant: Airbus Operations GmbH, Hamburg (DE)

(72) Inventor: Roelant Van Der Bos, Hamburg (DE)

(73) Assignee: Airbus Operations GmbH (DE)

( * ) Notice: Subject to any disclaimer, the term of this patent is extended or adjusted under 35 U.S.C. 154(b) by 162 days.

(21) Appl. No.: 14/465,885

(22) Filed: Aug. 22, 2014

(65) Prior Publication Data

US 2015/0052970 A1    Feb. 26, 2015

(30) Foreign Application Priority Data

Aug. 26, 2013   (DE) ........................ 10 2013 216 920

(51) Int. Cl.

| | |
|---|---|
| G01M 7/00 | (2006.01) |
| G01N 3/30 | (2006.01) |
| G01N 3/32 | (2006.01) |
| G01N 3/08 | (2006.01) |
| G01N 3/00 | (2006.01) |
| G01N 19/02 | (2006.01) |
| B64F 5/00 | (2006.01) |
| G01N 3/303 | (2006.01) |

(52) U.S. Cl.
CPC ............ *B64F 5/0045* (2013.01); *G01N 3/303* (2013.01); *G01N 2203/0033* (2013.01); *G01N 2203/04* (2013.01)

(58) Field of Classification Search
None
See application file for complete search history.

(56) References Cited

U.S. PATENT DOCUMENTS

| | | | |
|---|---|---|---|
| 2,656,711 A | 10/1953 | Tschudi | |
| 5,567,867 A * | 10/1996 | Nazar | G01M 7/08 173/90 |
| 6,374,661 B1 | 4/2002 | Buratynski et al. | |
| 6,807,841 B1 * | 10/2004 | Chen | G01N 3/303 73/12.06 |
| 7,367,212 B2 * | 5/2008 | Goyal | G01N 3/30 73/12.04 |
| 8,443,651 B2 * | 5/2013 | Le | G01M 7/08 73/12.06 |
| 8,453,490 B2 * | 6/2013 | Le | G01M 7/08 73/12.06 |

FOREIGN PATENT DOCUMENTS

| | | |
|---|---|---|
| DE | 23 32 212 A1 | 1/1975 |
| JP | 2001 091431 A | 4/2001 |

OTHER PUBLICATIONS

DE Search Report (Mar. 19, 2014) (10 2013 216 920.5).

* cited by examiner

*Primary Examiner* — Peter Macchiarolo
*Assistant Examiner* — Jermaine Jenkins
(74) *Attorney, Agent, or Firm* — Lerner, David, Littenberg, Krumholz & Mentlik, LLP

(57) ABSTRACT

A drop test device includes a suspension frame, a delay roller which is placed and mounted on the suspension frame, and at least one suspension cable, a first end of which is connected in a stationary manner to an attachment point on the outer surface of the delay roller and a second end of which includes a mounting which can be releasably or fixedly connected to a drop object.

11 Claims, 2 Drawing Sheets

DROP TEST DEVICE AND METHOD FOR CARRYING OUT A DROP TEST

FIELD OF THE INVENTION

The present invention relates to a drop test device and to a method for carrying out a drop test, in particular for testing the structural integrity of components for aircraft under crash conditions.

BACKGROUND OF THE INVENTION

Drop tests are usually carried out to determine the effects of an impact on the structure and integrity of objects to be analysed. A drop object is left to fall freely under predetermined constraints until it strikes an impact surface. The impact and the results thereof on the structure of the drop object can subsequently be analysed by way of sensor-based evaluations during the fall and analysis of the drop object after the fall.

In conventional drop tests, in particular aircraft components such as fuselage structural elements are lifted to a predetermined height from where they are left to fall freely. As a result of the mass distribution and the aerodynamic properties of the aircraft components, it may occur that the relative position of the aircraft component varies substantially by comparison with the release position until the actual impact. This sometimes detracts from the reproducibility and predictive power of the drop tests. In particular in fuselage structural elements, variation between the actual and intended impact position can significantly influence the impact properties.

Previous solutions, such as those known from document U.S. Pat. No. 6,374,661 B1, comprise drop test devices in which the relative position of drop objects in space can be controlled using holding devices until shortly before the impact. Only shortly before or during the impact itself are the holding devices released so as to create the conditions for freefall. Solutions of this type require active supervision and control mechanisms, which increase the complexity and fault susceptibility.

BRIEF SUMMARY OF THE INVENTION

There may be a need for drop test devices in which the relative impact position of drop objects during impact can be controlled even better.

Therefore, a first aspect of the invention provides a drop test device comprising a suspension frame, a delay roller which is placed on the suspension frame or supported and mounted in some other way, and at least one suspension cable, a first end of which is connected in a stationary manner to an attachment point on the outer surface of the delay roller and a second end of which comprises a mounting which can be connected to a drop object.

Further, a second aspect of the invention provides a method for carrying out a drop test. The method comprises attaching a first end of a suspension cable in a stationary manner to the outer surface of a delay roller, which is placed on a suspension frame and blocked in rotation, rolling up the suspension cable at least in part on the delay roller, attaching a second end of the suspension cable, which comprises a mounting, to a drop object, and releasing the blocking of the delay roller, in such a way that the suspension cable unrolls under the weight of the drop object on the delay roller.

In one embodiment of the drop test device, the drop test device may further comprise at least one deflection roller attached to the suspension frame, the at least one suspension cable being deflected via the deflection roller. The use of deflection rollers means that the configuration of the drop test device can be varied for drop objects of different sizes without the need to vary the basic construction of the delay roller.

In a further embodiment of the drop test device, the at least one suspension cable may be rolled up at least in part on the delay roller and be configured to be unrolled from the delay roller during a drop test. This ensures a controlled fall, in such a way that the movement of the delay roller ensures that the drop object descends uniformly in terms of relative fall position, even if a plurality of suspension cables is used.

In a further embodiment of the drop test device, the mounting may comprise a hook, one end of which is connected to the at least one suspension cable and the other end of which comprises a latch device, which is configured to latch into a protruding element of the drop object and block it in the falling direction. The use of hooks is particularly advantageous, since the drop object is only blocked in the falling direction. In the event of an impact, the suspension cables together with the hook move further in the fall direction, in such a way that the drop object is released and the impact is not influenced, or at least not substantially so, by the suspension ropes.

Alternatively, a latch element may also be provided on the mounting and a hook may also be provided on the drop object, in such a way that the latch element latches into the hook of the drop object.

In a further embodiment of the drop test device, the delay roller may comprise a projection or hook on the attachment point, the at least one suspension cable comprising a connection eye or protruding element on the first end, and the connection eye being pulled via the projection. In a variant of the drop test device according to the invention, the projection may be attached to the delay roller in such a way that during the drop test the connection eye releases from the projection after the suspension cable unrolls. This advantageously makes it possible to implement an additional safety mechanism to ensure that the impact of the drop object is influenced as little as possible by the drop device, since the suspension cables can slip from the delay roller after the fall and no longer have a blocking effect on the drop object.

In a further embodiment of the drop test device, the drop test device may comprise two or more suspension cables, of which a first end in each case is connected in a stationary manner to an attachment point on the outer surface of the delay roller at a uniform diameter, and a second end in each case comprises mountings which can be connected to four opposite sides or edges of the drop object. As a result, the orientation of the drop object can be ensured, in particular for cuboid or tubular components, without it being possible for a change in the relative fall positions with respect to the fall direction, in other words a rotation of the drop object, to occur during a fall.

In the same way, by using a delay roller having attachment points on the outer surface at a non-uniform diameter, controllable rotation about the horizontal axis can be produced.

In one embodiment of the method, the suspension cable can be deflected via at least one deflection roller, attached to the suspension frame, during the fall of the drop object.

In a further embodiment of the method, the mounting may comprise a hook, one end of which is connected to the at least one suspension cable and the other end of which comprises a latch device, the latch device being latched onto a protruding element of the drop object when the suspension cable is attached to the drop object, and blocking the drop object in the falling direction.

Alternatively, a latch element may also be provided on the mounting and a hook may also be provided on the drop object, in such a way that the latch element latches into the hook of the drop object.

In a further embodiment of the method, the delay roller may comprise a projection or hook, and the suspension cable may comprise a connection eye or protruding element at the first end, which is pulled via the projection when the first end of the suspension cable is attached to the delay roller. In one possible variant of the method, the projection may be attached to the delay roller in such a way that during the drop test the connection eye releases from the projection after the suspension cable unrolls.

BRIEF DESCRIPTION OF THE DRAWINGS

In the following, the invention is disclosed in greater detail in relation to and with reference to the embodiments shown in the accompanying drawings.

The accompanying drawings are for improved understanding of the present invention, and illustrate example variants of the invention. They are to illustrate principles, advantages, technical effects and possible variations. Naturally, other embodiments and many of the intended advantages of the invention are also conceivable, in particular in view of the detailed description of the invention in the following. The elements of the drawings are not necessarily shown to scale, and are shown in a simplified form or schematically in some cases for reasons of clarity. Like reference numerals denote like or equivalent components or elements.

DETAILED DESCRIPTION

Although special embodiments are disclosed and described herein, it is clear to the person skilled in the art that a wide range of further, alternative and/or equivalent implementations of the embodiments can be selected without substantially deviating from the basic concept of the present invention. In general, any variations on, modifications to and alterations to the embodiments disclosed herein should also be considered to be covered by the invention.

Figure 1:
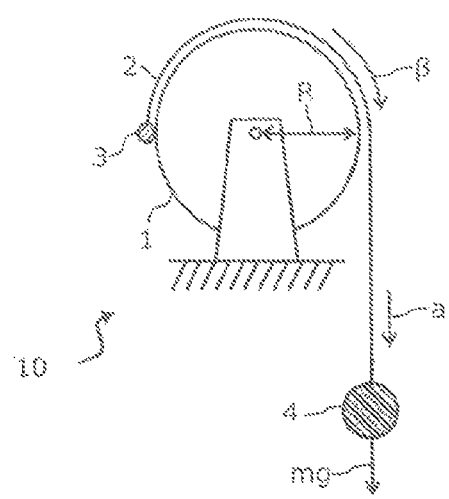
FIG. 1 is a schematic drawing of a drop test device in accordance with an embodiment of the invention.

FIG. 1 is a schematic drawing of a drop test device 10. The drop test device 10 comprises a delay roller having a roller radius R, which is formed as a fixed roller. The delay roller 1 can be mounted on a rotatably mounted axle, which is in turn fixed stationary with respect to a reference plane. A first end of a suspension cable 2 can be attached to an attachment point 3 on the outer surface of the delay roller 1 so as to be stationary with respect to the circumference of the delay roller 1. The suspension cable 2 itself is, at least in part, passed over or rolled onto the outer surface of the delay roller 1. For example, the suspension cable 2 is shown as merely being positioned against one outer surface portion, but it may also be possible to roll up the suspension cable 2 in more than one winding on the delay roller 1. The delay roller 1 may in particular have a uniform diameter over the roller. Alternatively, it may also be possible to use a delay roller having a non-uniform diameter. A second end of the suspension cable 2 is connected releasably or fixedly to a drop object 4, here shown schematically as a body having mass m. The weight mg of the drop object 4 biases the suspension cable 2 in the falling direction (downwards in FIG. 1) with respect to the roller axle when the delay roller 1 is blocked.

If the delay roller 1 is now released, in other words if the blocking is released, the drop object 4 moves downwards with an acceleration a under the influence of weight mg. As a result of the moment of inertia J of the delay roller, the drop object will move downwards with an acceleration a which is smaller than the acceleration due to gravity g in freefall, since part of the weight is being used for the rotational acceleration or angular acceleration $\beta$.

The following equation of movement applies (ignoring frictional forces and other energy losses in these schematic representations):

$$m \cdot g = m \cdot a + J \cdot \beta \cdot R^{-1}$$

Given the relationship between angular acceleration $\beta$ and linear acceleration a, this gives the following for the acceleration a:

$$a = m \cdot g / (m + J \cdot R^{-2})$$

This acceleration a is therefore smaller than the acceleration due to gravity g and the ratio thereof depends on the mechanical properties of the delay roller 1. In fall tests for components, for example fuselage structural elements, which can usually weigh between several hundred kilograms and several tonnes, the acceleration a can be controlled by suitable selection of the delay roller 1.

Figure 2:
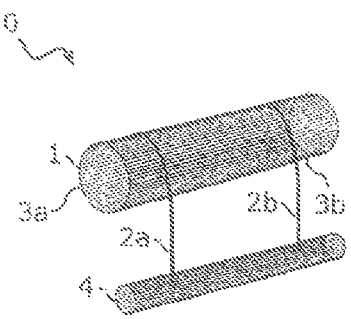
FIG. 2 is a schematic drawing of a further drop test device in accordance with a further embodiment of the invention.

As is shown in FIG. 2, two or more suspension cables 2a and 2b may be used, which are attached to the same delay roller 1. This results in a mechanical forced coupling between the suspension cables 2a, 2b, in such a way that the unrolling acceleration of the two suspension cables 2a, 2b is coupled to the rotational speed of the delay roller 1. A uniform diameter of the delay roller 1 makes positionally stable suspension of the drop object possible, in other words undesired rotations about a horizontal axis of rotation of the drop object 4 can be prevented. By contrast, a carefully selected, non-uniform diameter of the attachment points 3a and 3b on the outer surface of the delay roller 1 makes controlled rotation of the drop object possible during the drop test.

For example, in drop objects 4 which are three-dimensional in form (or generally speaking convex in geometric shape), in which the centre of gravity is positioned within the boundaries of the drop object 4, three or more suspension cables may be used, which can be attached at different mounting points, spanning a plano-convexpolygon, of the drop object 4. It may be advantageous for all of the suspension cables to be of an identical length. Purely by way of example, the drawings each show four suspension cables, although any other number of suspension cables may also be possible.

Figure 3:
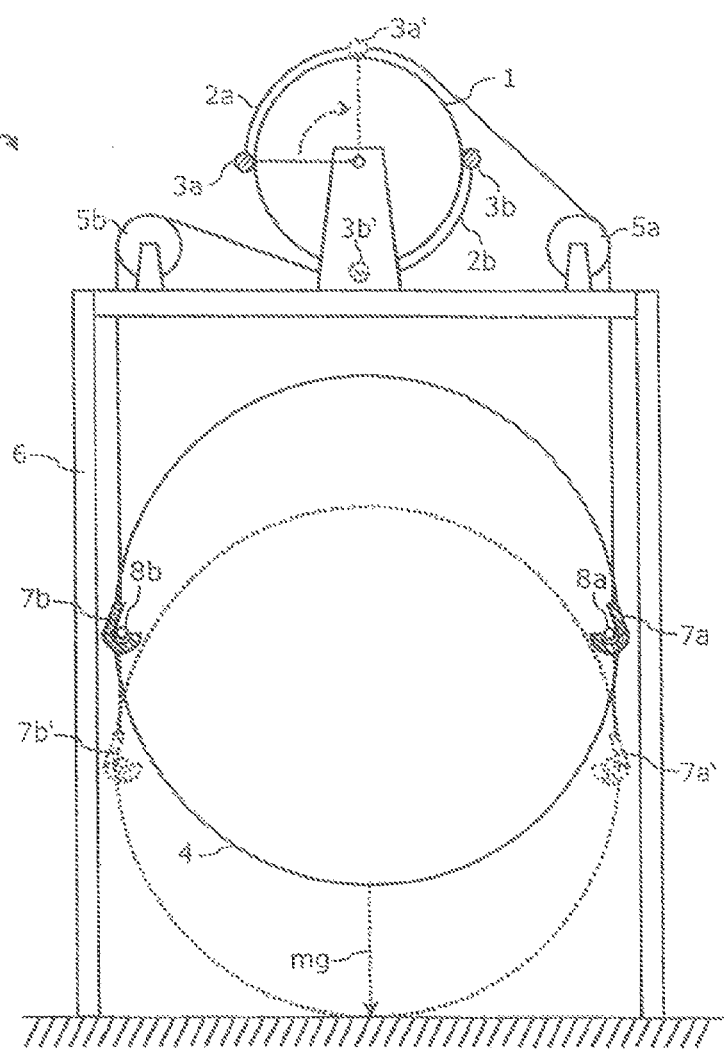
FIG. 3 is a schematic front view of a drop test device in accordance with a further embodiment of the invention.

FIG. 3 is a schematic front view of a drop test device 10. The drop device 10 comprises a suspension frame 6, shown by way of example with vertical frame supports and a suspension beam positioned horizontally on the frame supports. A delay roller 1 is placed on the suspension beam, in such a way that the mounting of the roller axis is fixed with respect to the suspension beam and thus with respect to the suspension frame 6. The drop test device 10 further comprises at least one suspension cable—in FIG. 3 two suspension cables 2a and 2b are shown by way of example—a first end of which is connected in a stationary manner to an attachment point 3a or 3b on the outer surface of the delay roller 1. The suspension cables 2a and 2b are rolled up at least in part on the delay roller 1, in such a way that during a drop test the rotation of the delay roller 1 about the roller axis causes the suspension cables 2a and 2b to unroll. The suspension cables 2a and 2b are each deflected via a deflection roller 5a or 5b attached in a stationary manner to the suspension frame 6, in such a way that the second ends thereof are guided vertically downwards, in other words in the falling direction of a drop object 4, from the deflection rollers 5a and 5b respectively.

At the second ends, the suspension cables 2a and 2b each comprise a mounting 7a or 7b, said mountings being connectable, releasably or fixedly, to the drop object 4. In the example of the FIG. 3, the mountings 7a and 7b are each hooks, one end of which is connected to a respective one of the suspension cables 2a and 2b. At the other end thereof, a latch device is provided which is configured to latch into a protruding element 8a or 8b of the drop object 4 and block it in the falling direction. The protruding elements 8a and 8b may for example be mechanically stable projections intrinsic to the structure of the drop object 4. However, it may also be possible to attach holding elements specially provided for drop tests, such as pins, bolts or other latch elements, which can engage in the latch device of the hooks 7a and 7b respectively as protruding elements 8a and 8b, to suitable mounting points on the drop object 4. Alternatively, a latch element may also be provided on the mounting 7a, 7b and a hook may also be provided on the drop object 4, in such a way that the latch element latches into the hook of the drop object 4.

In a drop test, the drop object 4 moves vertically downwards in the direction of the weight mg after the blocking of the delay roller 1 is released, in such a way that in the event of an impact on the ground or an impact plate provided for this purpose, the position shown in dashed lines in FIG. 3 is reached. In this position, the drop object 4 is braked by the impact, but the suspension cables 2a and 2b continue to move further downwards virtually unbraked, since the mountings 7a and 7b in the form of hooks do not provide any upward blocking effect for the drop object 4. The mountings 7a and 7b are therefore released from the protruding elements 8a and 8b in the positions 7a' and 7b', in such a way that the drop object 4 impacts substantially as in freefall. However, this has the advantage that the guidance by the suspension cables 2a, 2b prevents rotation of the drop object 4 about horizontal axes until the impact. As a result, the relative position of the drop object 4 can be controlled very well during impact, in such a way that the fall conditions remain reproducible and predictable.

The delay roller 1 may further comprise a projection on each of the attachment points 3a and 3b. The suspension cables 2a, 2b may be attached to these projections via connection eyes, which are pulled via the projections. An advantage of this type of attachment is that such projections can be attached to the delay roller 1 in such a way that in a drop test the connection eye is released from the projection after the suspension cable 2a or 2b unrolls. This may take place in that, in the impact position of the drop object 4, the attachment points 3a and 3b are located in the positions denoted by reference numerals 3a' and 3b' on the outer surface of the delay roller. If the projections make it possible for the connection eyes to slip off from the projections in these positions, the suspension cables 2a and 2b slide off from the delay roller 1, without an undesirable restraining force on the drop object 4 being maintained at the moment of the impact.

Figure 4:
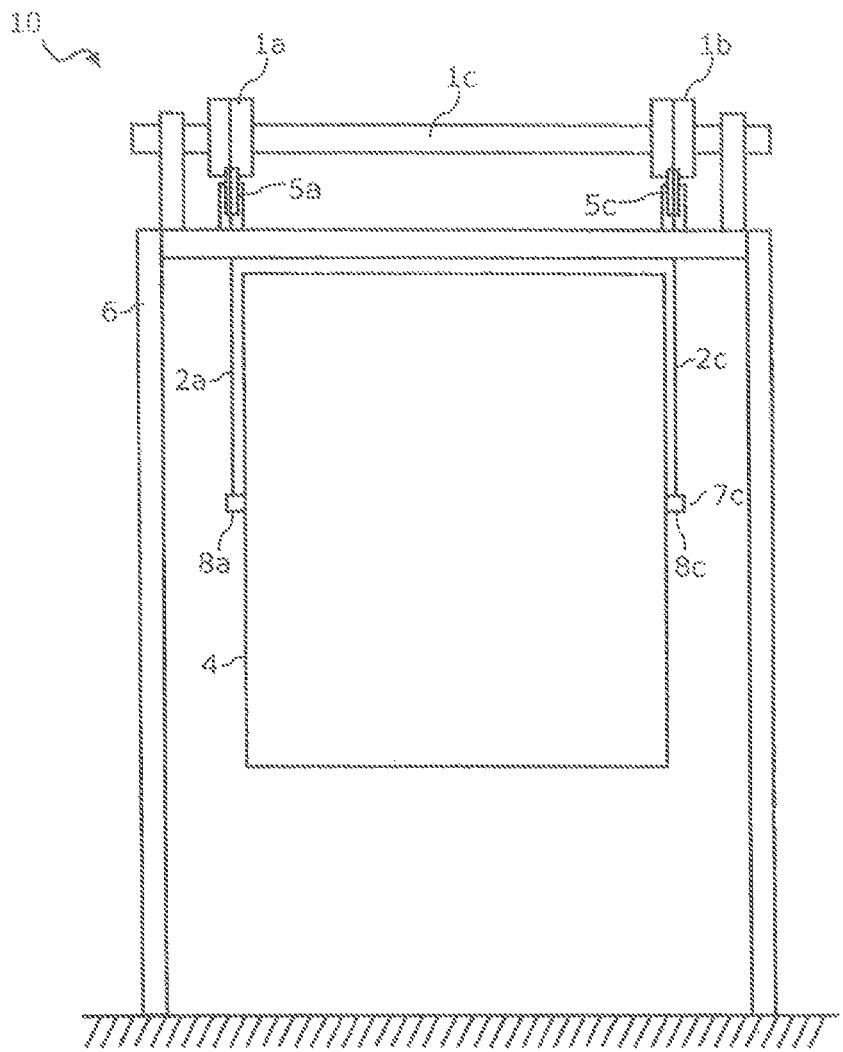
FIG. 4 is a schematic side view of the drop test device of FIG. 3.

FIG. 4 is a schematic side view of the drop test device 10 of FIG. 3. In particular, in FIG. 3 the delay roller axle 1c can be seen, on which the delay rollers 1a and 1b for the various side edges of the drop object 4 are rigidly connected and thus mechanically coupled. One of the rear suspension cables 2c is further shown, which is guided via a deflection roller 5c and releasably connected to a protruding element 8c on the rear face of the drop object 4 by way of a mounting 7c.

The drop test device 10 is suitable in particular for carrying out drop tests for aircraft components such as fuselage structural elements, aerofoil elements, turbines or similar aircraft components, in other words other components of all types.

Figure 5:
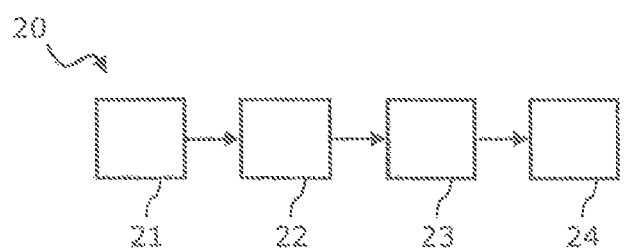
FIG. 5 is a schematic drawing of a method for carrying out a drop test in accordance with a further embodiment of the invention.

FIG. 5 is a schematic drawing of a method 20 for carrying out a drop test. The method 20 may in particular be carried out using the drop test device 10 shown by way of example in FIGS. 1 to 4.

In a first step 21, a first end of a suspension cable 2a, 2b is attached in a stationary manner to the outer surface of a delay roller 1, which is placed on a suspension frame 6 and blocked in rotation. The delay roller 1 may comprise a projection and the suspension cable 2a, 2b may comprise a connection eye or protruding element at the first end. The connection eye may be pulled via the projection during the attachment to the delay roller 1. The projection may be attached to the delay roller 1 in such a way that during a drop test the connection eye is released from the projection after the suspension cable 2a, 2b unrolls.

In a second step 22, the suspension cable 2a, 2b may be rolled up at least in part on the delay roller 1. The suspension cable 2a, 2b may subsequently be deflected via at least one deflection roller 5a, 5b attached to the suspension frame 6. In a third step 23, a second end of the suspension cable 2a, 2b is fixedly or releasably attached to a drop object 4. The second end of the suspension cable 2a, 2b comprises a mounting 7a, 7b, for example a hook, one end of which is connected to the suspension cable 2a, 2b and the other end of which comprises a latch device. The latch device may be latched onto a protruding element 8a, 8b of the drop object 4 when the suspension cable 2a, 2b is attached to the drop object 4, in such a way that the drop object 4 is blocked in the falling direction.

Finally, in a fourth step 24, the blocking of the delay roller 1 is released, in such a way that the suspension cable 2a, 2b unrolls on the delay roller 1 under the weight mg of the drop object 4. After a predetermined falling height of the drop object 4, the mountings 7a, 7b are released from the drop object 4 during the impact on the ground or a separate impact surface, in such a way that the drop object 4 impacts as if after freefall.

The invention claimed is:

1. A drop test device, comprising:
   a suspension frame;
   a delay roller placed and mounted on the suspension frame; and
   two or more suspension cables of which a first end in each case is connected in a stationary manner to a corresponding attachment point on the outer surface of the delay roller and a second end in each case comprises a mounting configured to be fixedly or releasably connected to a drop object.

2. The drop test device according to claim 1, further comprising:
   at least one deflection roller attached to the suspension frame,
   the two or more suspension cables being deflected via the deflection roller.

3. The drop test device according to claim 1, wherein the two or more suspension cables are rolled up at least in part on the delay roller and are configured to be unrolled from the delay roller during a drop test.

4. The drop test device according to claim 1, wherein the mountings comprise a hook, one end of which is connected to the corresponding suspension cable and the other end of which comprises a latch device, which is configured to latch into a protruding element of the drop object and block the drop object in the falling direction.

5. The drop test device according to claim 1, wherein the delay roller comprises a projection at the attachment point, the two or more suspension cables each comprising a connection eye or protruding element on the first ends, the connection eyes being pulled via the projection.

6. The drop test device according to claim 5, wherein the projection is attached to the delay roller in such a way that during the drop test the connection eye releases from the projection after the corresponding suspension cable unrolls.

7. A method for carrying out a drop test, comprising:
   attaching a first end of two or more suspension cables in each case in a stationary manner to the outer surface of a delay roller placed on a suspension frame and blocked in rotation;
   rolling up the two or more suspension cables at least in part on the delay roller;
   attaching a second end of the two or more suspension cables, the second ends each comprises a mounting, to a drop object; and
   releasing the blocking of the delay roller, in such a way that the two or more suspension cables unroll under the weight of the drop object on the delay roller.

8. The method according to claim 7, wherein the two or more suspension cables are deflected via at least one deflection roller, attached to the suspension frame, during the fall of the drop object.

9. The method according to claim 7, wherein the mountings each comprise a hook, one end of which is connected to the corresponding suspension cable and the other end of which comprises a latch device; and
   wherein the latch device is latched onto a protruding element of the drop object when the corresponding suspension cable is attached to the drop object, and blocks the drop object in the falling direction.

10. The method according to claim 7, wherein the delay roller comprises a projection, and wherein the two or more suspension cables each comprise a connection eye or protruding element at the first end, which is pulled via the projection when the first end of the corresponding suspension cable is attached to the delay roller.

11. The method according to claim 10, wherein the projection is attached to the delay roller in such a way that in a drop test the connection eye is released from the projection after the corresponding suspension cable unrolls.

* * * * *